US006881868B2

(12) United States Patent
Stutz et al.

(10) Patent No.: US 6,881,868 B2
(45) Date of Patent: Apr. 19, 2005

(54) PROCESS FOR THE PREPARATION OF (R)-2-ALKYL-3-PHENYL-1-PROPANOLS

(75) Inventors: Stefan Stutz, Basel (CH); Peter Herold, Basel (CH); Felix Spindler, Starrkirch-Wil (CH); Walter Weissensteiner, Mödling (AT); Thomas Sturm, Vienna (AT)

(73) Assignee: Speedel Pharma AG, Basel (CH)

( * ) Notice: Subject to any disclaimer, the term of this patent is extended or adjusted under 35 U.S.C. 154(b) by 0 days.

(21) Appl. No.: 10/312,992

(22) PCT Filed: Jun. 26, 2001

(86) PCT No.: PCT/CH01/00398

§ 371 (c)(1),
(2), (4) Date: Jan. 3, 2003

(87) PCT Pub. No.: WO02/02487

PCT Pub. Date: Jan. 10, 2002

(65) Prior Publication Data

US 2004/0092766 A1 May 13, 2004

(51) Int. Cl.$^7$ ............................................. C07C 41/18

(52) U.S. Cl. .................. 568/608; 568/610; 568/630; 568/648; 568/649; 568/651; 568/656; 568/658; 568/715; 568/812; 560/55; 560/60; 560/64

(58) Field of Search ................................. 568/608, 610, 568/630, 648, 649, 651, 656, 658, 715, 812; 560/55, 60, 64

(56) References Cited

U.S. PATENT DOCUMENTS

| 4,767,768 A | | 8/1988 | Okamoto et al. ............ 514/315 |
| 5,723,642 A | * | 3/1998 | Sturmer et al. ................ 556/18 |

FOREIGN PATENT DOCUMENTS

| DE | 195 16 968 A1 | * | 11/1996 | ............. C07F/9/50 |
| JP | 406025093 A | * | 2/1994 | ......... C07C/69/732 |

OTHER PUBLICATIONS

Bhatia et al., Synthesis of 1-(4'-Methoxy-1'-phenyl)allyl Citronellyl Ether and Related Substances, Journal of Indian Chemical Society, vol. 64(7), Jul. 1987, pp. 411–413.*
Hulskamper et al., Mechanism of the Substitution at the Cyclopropane Ring, Chemische Berichte, May 1981, vol. 114(2),pp. 746–756.*
Knsomasekharan et al.,Conformational Analysis of 1,1, 2–Trisubstituted Ethanes by PMR Part 1–3–Aryl–2–methylpropanols, Indian Journal of Chemistry, Section B: Organic Chemistry Including Medicinal Chemistry, vol. 27B(1), Jan. 1988, pp. 29–37.*
Journal o f the Indian Chemical Society, 1987, 64(7), pp. 411–413.*
Chemische Berichte, 1981, 114(2), pp. 746–756.*
Ger. Offen., Nov. 1996, 19516968.*
Indian Journal of Chemistry, Section B: Organic Chemistry Including Medicinal Chemistry, 1988, 27B(1), pp. 29–37.*
R. Schmid, et al.: "Axially dissymmetric diphosphines in the biphenyl series: synthesis of (6,6'–dimethoxybiphenyl–2, 2'–diyl) bis (diphenylphosphine) ('MeO–BIPHEP') and analogs via an ortho–lithiation/iodination Ullmlann–reaction approach", HELVETICA CHIMICA ACTA, vol. 74, No. 2, Mar. 13, 1991, pp. 370–389, XP002097708, Verlag Helvetica Chimica Acta, Basel, CH.
Y. Wei, et al.: "Aldol addition reaction of a lithium ester enolate in the solid state", Tetrahedron Letters, vol. 32, No. 12, Mar. 18, 1991, pp. 1535–1538, XP002175158, Elsevier Science Publishers, Amsterdam, NL.
M. Taniguchi, et al.: "Stereoselective reduction of 2–methyl–3–oxo esters (or amides) with sodium borohydride catalyzed by managanese (II) chloride or tetrabutylammonium borohydride. A practical preparation of erythro—and threo–3–hydroxy–2–methyl esters (or amides)", TETRAHEDRON, vol. 49, No. 48, Nov. 26, 1993, pp. 11169–11182, XP002175159, Elsevier Science Publishers, Amsterdam, NL.
K. Von Auwers, et al.: "Über Cumarunone und Hydrindone" Berichte der Deutschen Chemischen Gesellschaft, vol. 52, 1919, pp. 92–113, XP002175160, Verlag Chemie, Weinheim, DE.
G. Bartoli, et al.: "An efficient procedure for the diastereoselective dehydration of beta–hydroxy carbonyl compounds by CeC13.7H20/Nal system", ORGANIC LETTERS, vol. 2, No. 13, Jun. 1, 2000, pp. 1791–1793, XP002175161, American Chemical Society, Washington, DC.
G.W. Daub, et al.: "Acyclic stereoselection in the ortho ester Claisen rearrangement", JOURNAL of ORGANIC CHEMISTRY, vol. 62, No. 7, Apr. 4, 1997, pp. 1976–1985, XP002175162 American Chemical Society, Washington, DC, US.
H. Brunner, et al.: "Hydrierung prochiarler Olefine mit Rhodium–Komplexen von optisch aktiven Amidinen", MONATSHEFTE FÜR CHEMIE, vol. 111, No. 1, 1980, pp. 275–287, XP002175163 Springer Verlag, Vienna AT.

(Continued)

*Primary Examiner*—Rosalynd Keys
(74) *Attorney, Agent, or Firm*—Wenderoth, Lind & Ponack, L.L.P.

(57) ABSTRACT

Compounds of formula (I), wherein $R_1$ and $R_2$ are, independently of one another, H, $C_1$–$C_6$alkyl, $C_1$–$C_6$halogenalkyl, $C_1$–$C_6$alkoxyl, $C_1$–$C_6$alkoxy-$C_1$–$C_6$alkyl, or $C_1$–$C_6$alkoxy-$C_1$–$C_6$alkyloxy, and $R_3$ is $C_1$–$C_6$alkyl, are obtainable in high yiedls by stereoselective addition of $R_3$-substituted propionic acid esters to $R_1$- and $R_2$-substituted benzaldehydes of formula R—CHO to form corresponding 3-R-3-hydroxy-2-$R_3$-propionic acid esters, conversion of the OH group to a leaving group, subsequent regioselective elimination to form 3-R-2-$R_3$-propenic acid esters, and reduction to corresponding 3-R-2-$R_3$-allyl alcohols and their enantioselective hydrogenation, wherein R is (a).

25 Claims, No Drawings

OTHER PUBLICATIONS

Liang Li, et al.: "Synthesis of 2–methyl–1, 4–naphthquinone–4–C14", Journal of the American Chemical Society, vol. 74, No. 16, Aug. 20, 1952, pp. 4089–4090, XP002175164 American Chemical Society, Washington, DC., US.

M. Brunner, et al.: "The first stereoselective palladium–catalysed cyclocarbonylation of beta, gamma–substituted allylic alcohols", Journal of Organic Chemistry, vol. 62, No. 22, Oct. 31, 1997, pp. 7565–7568, XP002175165, American Chemical Society, Washington, DC, US.

M.D. Turnbull: "Productivity in synthesis: a mixture protocol to raise compound output is demonstrated for asymmetric cyclopropanation of allyl alcohols", Journal of the Chemical Society, Perkin Transactions 1, No. 8, Apr. 21, 1997, pp. 1241–1248, XP002175166, Royal Society of Chemistry, Letchworth, GB.

P. Gramatica, et al.: "Reduction of cinnamyl alcohols and cinnamaldehydes by *Saccharomyces cerevisiae*", Bioorganic Chemistry, vol. 10, No. 1, 1981, pp. 22–28, XP00105943, Academic Press, New York, NY, US.

J.K. Crandall, et al.: "Cis reduction of acetylanes by organocopper reagents ", Journal of Organic Chemistry, vol. 41, No. 26, Dec. 24, 1976, pp. 4089–4092, XP002175168, American Chemical Society, Washington, DC, US.

J.G. Duboudin et al.: "Réactifs de Grignard vinyliques gamma fonctionnels. I. Réactivité des organomagnésiens vis–à–vis d'alcools alpha acétyléniques en présnece d'halogénures cuivreux", Journal of Organometallic Chemistry, vol. 168, No. 1, Mar. 13, 1979, pp. 1–11, XP002028213, Elsevier Sequoia, Lausanne, CH.

D. Basavaiah, et al.: "Applications of Baylis–Hillman coupling products: a remarkable reversal of stereochemistry from esters to nitriles: a simple synthesis of (2E)–2–methylalk2–en–1–ols and (2Z)–2–methylalk–2–enenitriles", Journal of the Chemical Society, Chemical Communications., No. 13, Jul. 1, 1992, pp. 955–957, XP002175169, Royal Society of Chemistry, Letchworth, GB.

P.H. Boyle, et al., : "Reaction of ally and benzyl alcohols, and their toluene–p–sulphonates, with furan", Journal of the Chemical Society, Perkin Transactions 1, No. 13, 1972, pp. 1617–1622, XP002175170, Royal Society of Chemistry, Letchworth, GB.

A. Kamimura, et al.: "Stereoselective thio–Micheal/aldol tandem reaction to alpha, beta–unsaturated esters", Journal of Organic Chemistry, vol. 64, No. 17, Aug. 4, 1999, pp. 6353–6360, XP002175171, American Chemical Society, Washington, DC, US.

R. Inoue, et al.: "Reaction of tert–butyl dibromoacetate or N, N–diethyldibromoacetamide with trailkylmanganate providing an alkylated manganese enolate", Journal of Organic Chemistry, vol. 63, No. 4., Jan. 27, 1998, pp. 910–911, XP002175172, American Chemical Society, Washington, DC, US.

B.C. Ranu, et al.: "Surface–mediated solid phase reaction. Part 9. A convenient procedure for aldol reaction of ketene silyl acetals with aldehydes on the solid surface of alumina", Synthetic Communications, vol. 27, No. 17, 1997, pp. 3065–3077, XP001015930, Marcel Dekker, Basel, CH.

P.M. Bodnar, et al.: "Stereo—and regioselectivity of reactions of siliranes with aldehydes and related substrates", Journal of Organic Chemistry, vol. 62, No. 14, Jul. 11, 1997, pp. 4737–4745, XP002175174, American Chemical Society, Washington, DC, US.

J. Ezquerra, et al.: "(S)–Ethyl 4,4–dimethyl pyroglutamate as a new ' quat' chiral auxiliary in aldol condensations" Tetrahedron: Asymmetry, vol. 8, No. 5, Mar. 13, 1997, pp. 669–671, XP004055877, Elsevier Science Publishers, Amsterdam, NL.

K. Takai et al.: "Sequential generation and utilisation of radical and anionic species with a novel manganese–lead reducing agent. Three–component coupling reactions of alkyl iodides, electron–deficient olefins, and carbonyl compounds", Journal of Organic Chemistry, vol. 61, No. 23, Nov. 15, 1996, pp. 7990–7991, XP002175175, American Chemical Society, Washington, DC, US.

Y Han, et al.: "Metallic gallium–promoted Reformatskytype reaction", Chinese Chemical Letters, vol. 7, No. 8, 1996, pp. 713–716, XP001015981, Chinese Chemical Bureau, Beijing, CN.

J.J. Juarez –Brambila et al.: "Use of mesityllithium in the alpha–alkylation reaction of B–alkyl–9–borabicyclo'3.3.1Inonanes", Journal of the Indian Institute of Sciences, vol. 74, No. 1, Jan. 1994, pp. 7–13, XP00105935.

K. Ganesan, et al.: Enolboration. 6. Dicyclohexyliodoborane, a versatile reagent for the steroselective synthesis of either Z or E enolates from representative esters:, Journal of Organic Chemistry, vol. 59, No. 9, May 6, 1994, pp. 2336–2340, XP002175178, American Chemical Society, Washington, DC, US.

C.R. Sarko, et al.: "Chelatio–controlled protocol for the diasterioselective reduction of ketones", Journal of Organic Chemistry, vol. 59, No. 4, Feb. 25, 1994, pp. 705–706, XP002175179, American Chemical Society, Washington, DC, US.

E.J. Corey et al.: "Versatile chiral agent for the highly anatioselective synthesis of either anti or syn ester aldols", Journal of the American Chemical Society, vol. 112, No. 12, Jun. 6, 1990, pp. 4976–4977, XP002175180, American Chemical Society, Washington, DC, US.

H. Akita, et al.: "A highly stereoselective synthesis of the versatile chiral synthons possessing two sterogenic centres, the formal total synthesis of (−)–oudemansins A, B, and X", Tetrahedron: Asymmetry, vol. 5, No. 7, Jul. 1994, pp. 1207–1210, XP002175181, Elsevier Science Publishers, Amsterdam, NL.

D. –W. Su, et al.: "A novel DMAP–promoted oxazolidinethione deacylation. Application for the direct conversion of the initial chiral thioimide aldols to various ester protecting groups", Tetrahedron Letters, vol. 40, No. 22, May 28, 1999, pp. 4197–4198, XP004164696, Elsevier Science Publishers, Amsterdam, NL.

W. Oppolzer, et al.: "Bornanesultam–directed asymmetric synthesis of crystalline, enatiomerically pure syn aldols", Journal of the American Chemical Society, vol. 112, No. 7, Mar. 28, 1990, pp. 2767–2772, XP 002175182, American Chemical Society, Washington, DC US.

T. Yamada, et al.: "A preparative method of DL–threo–3–isopropylmalic acid and DL–threo–'2–2HI–3–isopropylmalic acid", Chemistry Letters, No. 9, Sep. 1987, pp. 1745–1748, XP002175183, Chemistry Society of Japan, Tokyo, JP.

A. Balsamo et al.: "Structure–activity realationship in cinnamides.3. Synthesis and anticonvulsant activity evaluation of some derivatives of (E)– and (Z)–m–(trifluormethyl)cinnamides", Journal of Medicinal Chemistry, vol. 24,, No. 5, May 1981, pp. 525–532, XP002175184, American Chemical Society, Washington, DC, US.

C.H. Heathcock, et al.: "Acyclic stereoselection. 11. Double stereodifferentiation as a method for achieving superior Cram's rule selectivity in aldol condensations with chiral aldehydes", Journal of Organic Chemistry, vol. 46, No. 7, Mar. 27, 1981, pp. 1296–1309, XP002175185, American Chemical Society, Washington, DC, US.

J. Canceill, et al.: "Sur la stéréochimie de la réformatsky. II. Spectres IR et spectres RMN des béta–hydroxyesters obtenus. Dosage de leurs mélanges. Bilan des résultats", Bulletin de la Societe Chimique de France, No. 3, 1967, pp. 1024–1030, XP002175186, Société francaise de chimie, Paris, FR.

* cited by examiner

PROCESS FOR THE PREPARATION OF (R)-2-ALKYL-3-PHENYL-1-PROPANOLS

The invention relates to a stereoselective process for the preparation of (R)-2-alkyl-3-phenyl-1-propanols and new intermediate products obtained in the process steps.

In EP-A-0 678 503, δ-amino-γ-hydroxy-ω-aryl-alkanecarboxamides are described which exhibit renin-inhibiting properties and could be used as antihypertensive agents in pharmaceutical preparations. The manufacturing processes described are unsatisfactory in terms of the number of process steps and yields and are not suitable for an industrial process. A disadvantage of these processes is also that the total yields of pure diastereomers that are obtainable are too small.

In a new process, one starts from 2,7-dialkyl-8-aryl-4-octenoyl amides, whose double bond is simultaneously halogenated in the 5-position and hydroxylated in the 4-position under lactonization, then the halogen is substituted by azide, the lactone amidated and the azide then transferred to the amine group. The desired alkanecarboxamides are obtained with the new process both in high total yields and in a high degree of purity, and selectively pure diastereomers can be prepared. The halolactonization of process step a), the azidation of process step b), and the azide reduction of process step d) are described by P. Herold in the Journal of Organic Chemistry, Vol. 54 (1989), pages 1178-1185.

The 2,7-dialkyl-8-aryl-4-octenoyl amides may correspond for example to formula A,

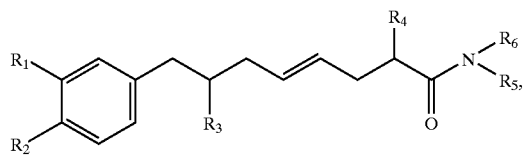

(A)

and especially to formula A1

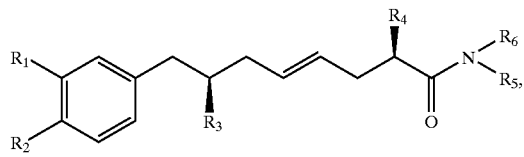

(A1)

wherein $R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, $R_6$ is $C_1$–$C_6$alkyl, $R_5$ is $C_1$–$C_6$alkyl or $C_1$–$C_6$alkoxy, or $R_5$ and $R_6$ together are tetramethylene, pentamethylene, 3-oxa-1,5-pentylene or —$CH_2CH_2O$—C(O)— substituted if necessary with $C_1$–$C_4$alkyl, phenyl or benzyl.

The compounds of formulae A and A1 are obtainable by reacting a compound of formula B

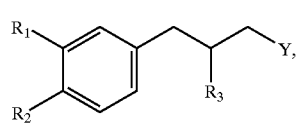

(B)

as racemate or enantiomer, with a compound of formula C, as racemate or enantiomer,

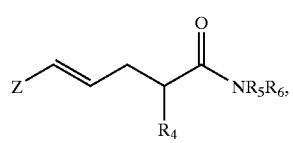

(C)

wherein $R_1$ to $R_4$, $R_5$ and $R_6$ are as defined above, Y is Cl, Br or I and Z is Cl, Br or I, in the presence of an alkali metal or alkaline earth metal. Y and Z are preferably Br and especially Cl.

The compounds of formula B are known from EP-A-0 678 503. The compounds of formula C may be prepared from amidation of the corresponding carbonic esters, amides, or halides. The formation of carboxamides from carbonic esters and amines in the presence of trialkyl aluminium or dialkyl aluminium halide, for example using trimethyl aluminium or dimethyl aluminium chloride, is described by S. M. Weinreb in Org. Synthesis, VI, page 49 (1988). The carbonic esters are obtainable by the reaction of trans-1,3-dihalogenpropene (for example, trans-1,3-dichlorepropene) with corresponding carbonic esters in the presence of strong bases, for example alkali metal amides.

A satisfactory solution for the stereoselective preparation of compounds of formula B has not yet been found, especially with regard to an industrial process. Surprisingly it has now been found that 2-alkyl-3-phenylpropionic acids can be stereoselectively prepared with high yields in only three process steps. When suitably substituted benzaldehydes are condensed with carbonic esters to form 2-alkyl-3-hydroxy-3-phenylpropionic acid esters, the desired diastereomers are obtainable in surprisingly high yields mostly as crystalline compounds which can be readily isolated. After conversion of the hydroxy group to a leaving group, 2-alkylcinnamic acid esters are then formed by elimination with strong bases with surprisingly high regioselectivity. The allyl alcohols obtained after hydrogenation can in turn be hydrogenated in the presence of certain catalysts to form practically enantiomer-pure 2-alkyl-3-phenyl-1-propanols. These alcohols can then be converted by halogenation to the compounds of formula B in a manner known per se.

The object of the invention is a process for the preparation of compounds of formula I,

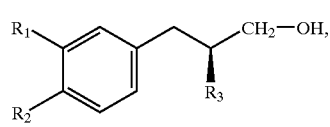

(I)

wherein $R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$-alkyl, or $C_1$–$C_6$alkoxy-$C_1$–$C_6$alkyloxy, and $R_3$ is $C_1$–$C_6$-alkyl, comprising a) the reaction of a compound of formula II

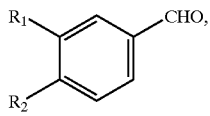

(II)

wherein $R_1$ and $R_2$ are as defined above, with a compound of formula III,

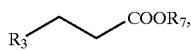

(III)

wherein $R_3$ is as defined above, to form a compound of formula IV,

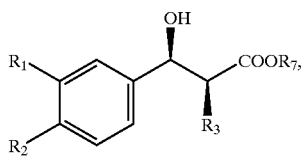

(IV)

wherein $R_7$ is $C_1$–$C_{12}$alkyl, $C_3$–$C_8$cycloalkyl, phenyl or benzyl, b) the isolation of the crystalline compound of formula IV, the conversion of the OH group to a leaving group, and the reaction of a compound containing a leaving group in the presence of a strong base to form a compound of formula V,

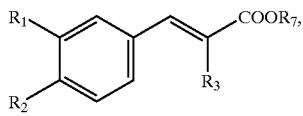

(V)

c) the reduction of carbonic esters of formula V to form the alcohol of formula VI,

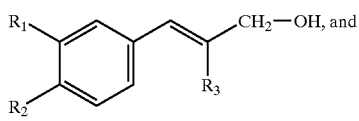

(VI)

d) the hydrogenation of the alcohol of formula VI in the presence of hydrogen and catalytic quantities of a metal complex as asymmetric hydrogenation catalyst, comprising metals from the group of ruthenium, rhodium and iridium, to which the chiral bidentate ligands are bonded, to form a compound of formula I.

$R_1$ and $R_2$ may be a linear or branched alkyl and preferably comprise 1 to 4 C atoms. Examples are methyl, ethyl, n- and i-propyl, n-, i- and t-butyl, pentyl and hexyl.

$R_1$ and $R_2$ may be a linear or branched halogenalkyl and preferably comprise 1 to 4 C atoms, 1 or 2 C atoms being especially preferred. Examples are fluoromethyl, difluoromethyl, trifluoromethyl, chloromethyl, dichloromethyl, trichloromethyl, 2-chloroethyl and 2,2,2-trifluoroethyl.

$R_1$ and $R_2$ may be a linear or branched alkoxy and preferably comprise 1 to 4 C atoms. Examples are methoxy, ethoxy, n- and i-propyloxy, n-, i- and t-butyloxy, pentyloxy and hexyloxy.

$R_1$ and $R_2$ may be a linear or branched alkoxyalkyl. The alkoxy group preferably comprises 1 to 4 and especially 1 or 2 C atoms, and the alkyl group preferably comprises 1 to 4 C atoms. Examples are methoxymethyl, 1-methoxyeth-2-yl, 1-methoxyprop-3-yl, 1-methoxybut-4-yl, methoxypentyl, methoxyhexyl, ethoxymethyl, 1-ethoxyeth-2-yl, 1-ethoxyprop-3-yl, 1-ethoxybut-4-yl, ethoxypentyl, ethoxyhexyl, propyloxymethyl, butyloxymethyl, 1-propyloxyeth-2-yl and 1-butyloxyeth-2-yl.

$R_1$ and $R_2$ may be linear or branched $C_1$–$C_6$alkoxy-$C_1$–$C_6$alkyloxy. The alkoxy group preferably comprises 1 to 4 and especially 1 or 2 C atoms, and the alkyloxy group preferably comprises 1 to 4 C atoms. Examples are methoxymethyloxy, 1-methoxyeth-2-yloxy, 1-methoxyprop-3-yloxy, 1-methoxybut-4-yloxy, methoxypentyloxy, methoxyhexyloxy, ethoxymethyloxy, 1-ethoxyeth-2-yloxy, 1-ethoxyprop-3-yloxy, 1-ethoxybut-4-yloxy, ethoxypentyloxy, ethoxyhexyloxy, propyloxymethyloxy, butyloxymethyloxy, 1-propyloxyeth-2-yloxy and 1-butyloxyeth-2-yloxy.

In a preferred embodiment, $R_1$ is methoxy-$C_1$–$C_4$alkyloxy or ethoxy-$C_1$–$C_4$alkyloxy, and $R_2$ is preferably methoxy or ethoxy. Quite especially preferred are compounds of formula I, wherein $R_1$ is 1-methoxyprop-3-yloxy and $R_2$ is methoxy.

$R_3$ may be a linear or branched alkyl and preferably comprise 1 to 4 C atoms. Examples are methyl, ethyl, n- and i-propyl, n-, i- and t-butyl, pentyl and hexyl. In a preferred embodiment, $R_3$ in compounds of formula I is isopropyl.

Especially preferred are compounds of formula I wherein $R_1$ is methoxy-n-propoxy, $R_2$ is methoxy and $R_3$ is isopropyl.

$R_7$ is preferably $C_1$–$C_6$alkyl, $C_1$–$C_4$alkyl being especially preferred; some examples are methyl, ethyl, n-propyl and n-butyl.

The starting compounds of formulae II and III used in process step a) are known or can be prepared in a manner similar to known processes. Compounds of formula II are described in EP-A 0 678 503. The reaction is advantageously carried out at low temperatures, for example 0–40° C., in the presence of at least equivalent quantities of strong bases. The reaction is further expediently carried out in a solvent, ethers such as diethyl ether, tetrahydrofuran and dioxane being especially suitable. Suitable strong bases are in particular alkali metal alcoholates and secondary amides, such as lithium diisopropylamide.

The desired diastereomer of formula IV is surprisingly formed up to about 75%. The compounds of formula IV are surprisingly crystalline and can therefore be readily isolated without any substantial losses by means of extraction and crystallization.

The conversion of the OH group to a leaving group in reaction step b) is known per se. Reaction with carboxylic acids or sulfonic acids, or their anhydrides (acylation), is especially suitable. Some examples of carboxylic acids are formic acid, acetic acid, propionic acid, benzoic acid, benzenesulfonic acid, toluenesulfonic acid, methylsulfonic acid and trifluoromethylsulfonic acid. The use of acetic acid anhydride has proved especially successful. The elimination is expediently carried out in the presence of strong bases, alkali metal alcoholates such as potassium t-butylate being especially suitable. The presence of solvents such as ethers is expedient. The reaction is advantageously carried out at low temperatures, for example 0–40° C. It is of advantage to conduct the elimination reaction directly in the reaction mixture for acylation. The elimination leads to the desired Z isomers with surprisingly high regioselectivity. These isomers are crystalline and can therefore be readily isolated without any substantial losses by means of extraction and crystallization. The yields are above 80%.

Process step c) is preferably carried out at low temperatures, for example −40° C. to 0° C., and advantageously in a solvent. Suitable solvents are, for example, hydrocarbons (pentane, cyclohexane, methylcyclohexane, benzene, toluene and xylene). For hydrogenation, metal hydrides are expediently used in at least equimolar quantities, for example LiH, NaH, NaBH$_4$, LiAlH$_4$, and alkyl metal hydrides such as methyl, ethyl, or isopropyl aluminium dihydride or tin trihydride, dimethyl, diethyl, triisopropyl or triisobutyl aluminium hydride or tin dihydride, and tributyl tin hydride. The compounds can be isolated by means of extraction and purified by means of distillation. The yields amount to more than 90%.

The asymmetric hydrogenation in process step d) of α,β-unsaturated carboxylic acids with homogeneous, asymmetric hydrogenation catalysts is known per se and described for example by John M. Brown in E. Jacobsen, A. Pfaltz, H. Yamamoto (Eds.), Comprehensive Asymmetric Catalysis I to III, Springer Verlag, 1999, pages 121 to 182. Especially effective are ruthenium and rhodium catalysts. Chiral ditertiary diphosphines whose phosphine groups in the 1,2, 1,3 or 1,4 position are bonded to a $C_2$–$C_4$carbon chain are often used as ligands. The skeletal structures of the chiral ditertiary diphosphines may be acyclic, monocyclic or polycyclic. The phosphine groups may be substituted with the same or with different, preferably the same, substituents selected from the group of $C_1$–$C_8$alkyl, $C_3$–$C_8$cycloalkyl, $C_6$–$C_{12}$aryl, and $C_6$–$C_{12}$aryl-$C_1$–$C_4$alkyl. Cycloalkyl and aryl may be unsubstituted or substituted with $C_1$–$C_4$alkyl, $C_1$–$C_4$alkoxy, $C_1$–$C_4$fluoroalkyl or C-$C_{12}$secondary amino. Suitable phosphine groups are also phosphanyl, preferably five-member phosphanyl, which if necessary is substituted in one or both α-positions with $C_1$–$C_4$alkyl or $C_1$–$C_4$alkoxy.

Some examples of chiral ditertiary diphosphines are (R"$_2$P is for example diphenylphosphino or dicyclohexylphosphino, substituted if necessary) 1,2-Di-R"$_2$P-propane, 2,3-Di-R"$_2$P-butane, 1,2-Di-R"$_2$P-norbornane or -norbornadiene, 1,2-Di-R"$_2$P-cyclopentane, 1,2-Di-R"$_2$P—N-methylpyrrolidine, 2,2'-Di-R"$_2$P-biphenyl or -binaphthyl, 2,2'-Di-R"$_2$P-6-methyl or -6,6'-dimethylbiphenyl, 2,2'-Di-R"$_2$P-6-methoxy or -6,6'-dimethoxybiphenyl, and 1-(α-R"$_2$P-ethyl)-2-R"$_2$P-ferrocene.

Good optical yields are achieved using metal complexes of formula VII or VIIa,

[LMeYZ]     (VII)

[IMeY]⁺E⁻     (VIIa), wherein
Me is rhodium;
Y stands for two olefins or one diene;
Z is Cl, Br or I;
E⁻ is the anion of an oxygen acid or a complex acid; and
L is a chiral ligand from the group of ditertiary diphosphines, in which the phosphine groups are bonded to a $C_2$–$C_4$ chain of the diphosphine backbone chain, and the diphosphine forms a five to seven-member ring together with the rhodium atom.

Where Y stands for two olefins, they may be $C_2$–$C_{12}$ olefins, $C_2$–$C_6$olefins being preferred and $C_2$–$C_4$olefins being especially preferred. Examples are propene, but-1-ene and especially ethylene. The diene may comprise 5 to 12 and preferably 5 to 8 C atoms and may be an acyclic, cyclic or polycyclic diene. The two olefin groups of the diene are preferably linked by one or two $CH_2$ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y represents preferably two ethylene or 1,5-hexadiene, 1,5-cyclooctadiene or norbornadiene.

In formula VII, Z is preferably Cl or Br. Examples of $E_1$ are $ClO_4^-$, $CF_3SO_3^-$, $CH_3SO_3^-$, $HSO_4^-$, $BF_4^-$, $B(phenyl)_4^-$, $PF_6^-$, $SbCl_6^-$, $AsF_6^-$ or $SbF_6^-$.

It was found that ligands with a biphenyl backbone are especially suitable for the asymmetric hydrogenation of compounds of formula VI. With these ligands in the metal complexes of formulae VII and VIIa, optical yields of at least 95% ee can be achieved, which represents a substantial cost saving for manufacture on an industrial scale. In process step d), therefore, it is preferred to use metal complexes of formulae VII and VIIa, wherein L represents the ligands of formula VIII,

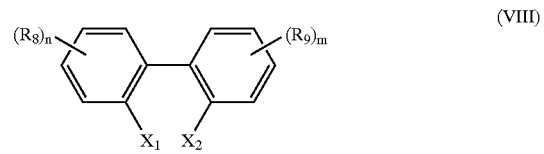

wherein
m and n in each case are 0 or an integer from 1 to 4, and $R_8$ and $R_9$ are hydrogen or the same or different substituents, selected from the $C_1$–$C_4$alkyl and $C_1$–$C_4$alkoxy group; and
$X_1$ and $X_2$ are, independently of one another, secondary phosphino.

Substituents are preferably bonded in the 6 position or the 6,6' positions.

As an alkyl, $R_8$ and $R_9$ may preferably comprise 1 to 2 C atoms. Linear alkyl is preferred. Examples of $R_8$ and $R_9$ as an alkyl are methyl, ethyl, n- and i-propyl, n-, i- and t-butyl. Methyl and ethyl are preferred, and methyl is especially preferred.

As an alkoxy, $R_8$ and $R_9$ may preferably comprise 1 to 2 C atoms. Linear alkoxy is preferred. Examples of $R_8$ and $R_9$ as an alkoxy are methoxy, ethoxy, n- and i-propoxy, n-, i- and t-butoxy. Methoxy and ethoxy are preferred and methoxy is especially preferred.

The $X_1$ and $X_2$ groups may be different or preferably the same and correspond to formula $PR_{10}R_{11}$, wherein $R_{10}$ and $R_{11}$ are the same or different and represent branched $C_3$–$C_8$alkyl, $C_3$–$C_8$cycloalkyl, or unsubstituted or phenyl substituted with one to three $C_1$–$C_4$alkyl, $C_1$–$C_4$-alkoxy, or —$CF_3$.

Special preference is for ligands of formulae VIII, wherein $X_1$ and $X_2$ are a $PR_{10}R_{11}$ group, wherein $R_{10}$ and $R_{11}$ in each case are cyclobutyl, cyclopentyl, cyclohexyl, phenyl or phenyl substituted with 1 or 2 methyl, methoxy or $CF_3$.

The metal complexes used as catalysts may be added as separately prepared isolated compounds, or also formed in situ before the reaction and then mixed with the substrate to be hydrogenated. It may be advantageous in the reaction using isolated metal complexes to add additional ligands, or in the in situ preparation to use surplus ligands. The surplus may for example be up to 10 moles and preferably 0.001 to 5 moles, based on the metal complexes used for the preparation.

Process step d) may be carried out at low or elevated temperatures, for example at temperatures from −20 to 150° C., preferably from −10 to 100° C., temperatures of 10 to 80° C. being especially preferred. The optical yields are generally better at low temperatures than at high temperatures.

The process according to the invention may be carried out at normal pressure or preferably under positive pressure. The pressure may for example range from $10^5$ to $2 \times 10^7$ Pa (Pascal).

Catalysts are preferably used in quantities from 0.0001 to 10 mol-% based on the compound to be hydrogenated, the range 0.001 to 10 mol-% being especially preferred and the range 0.01 to 5 mol-% being preferred in particular.

The preparation of catalysts as well as process step d) and the other process steps may be carried out in the absence or the presence of an inert solvent, wherein one solvent or a mixture of solvents may be used. Suitable solvents are, for example, aliphatic, cycloaliphatic and aromatic hydrocarbons (pentane, hexane, petroleum ether, cyclohexane, methylcyclohexane, benzene, toluene, xylene), aliphatic halogenated hydrocarbons (dichloromethane, chloroform, di- and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carbonic esters and lactones (ethyl or methyl acetate, valerolactone), N-substituted lactams (N-methylpyrrolidone), carboxamides (dimethylamide, dimethylformamide), acyclic ureas (dimethylimidazoline), and sulfoxides and sulfones (dimethyl sulfoxide, dimethyl sulfone, tetramethylene sulfoxide, tetramethylene sulfone) and alcohols (methanol, ethanol, propanol, butanol, ethylene glycol monomethyl ether, ethylene glycol monoethyl ether, diethylene glycol monomethyl ether) and water. The solvents may be used alone or in a combination of at least two solvents.

The reaction may be carried out in the presence of co-catalysts, for example quaternary ammonium halogenides (tetrabutylammonium iodide) and/or in the presence of protonic acids, for example mineral acids.

Using the regioselective and enantioselective process according to the invention, the intermediate products of the formula (B) may be prepared via all process steps in yields of at least 50% by weight, based on the compounds of formula II. The high total yields make the process suitable for industrial use.

A further object of the invention relates to the compounds (intermediates) of formula VI,

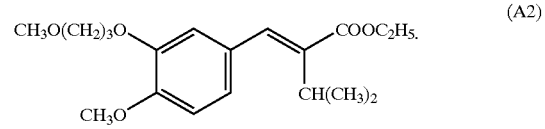

(VI)

wherein $R_1$, is methoxy-$C_1$–$C_4$alkyloxy or ethoxy-$C_1$–$C_4$alkyloxy, $R_2$ is methoxy or ethoxy, and $R_1$ is $C_1C_6$alkyl.

A further object of the invention relates to the compounds (intermediates) of formula IV,

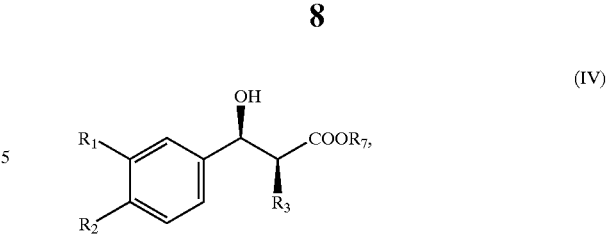

(IV)

wherein $R_1$ is methoxy-$C_1$–$C_4$alkyloxy or ethoxy-$C_1$–$C_4$alkyloxy, $R_2$ is methoxy or ethoxy, $R_3$ is $C_1$–$C_6$alkyl, and $R_7$ is $C_3$–$C_2$alkyl, $C_\#$–$C_8$cycloaxyl, phenyl or benzyl.

The embodiments and preferences described hereinabove apply for $R_1$, $R_2$, $R_3$ and $R_7$.

The following examples explain the invention in more detail.

A) Preparation of (R)-3-[4'-CH$_3$O-3'-(CH$_3$O(CH$_2$)$_3$O)-phen-1-yl]-2-isopropylpropan-1-ol (A4)

EXAMPLE A1

Preparation of

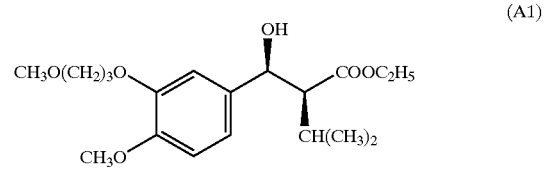

(A1)

A solution of 436 ml diisopropylamine and 2.6 l tetrahydrofuran is cooled to −20° C., and 1.234 l n-hexyl lithium (2.5 M in hexane) is added dropwise over a period of 15 minutes. A solution of 368 g ethyl isovalerate in 1.7 l tetrahydrofuran is added dropwise over a period of 15 minutes at −20° C. After a further 10 minutes, a solution of 584 g 4-methoxy-3-(3-methoxy-propoxy)benzaldehyde (EP 0 678 503) in 1.7 l tetrahydrofuran is added drop by drop and stirred for 40 minutes at −20° C. Then 2.15 l saturated aqueous ammonium chloride solution is added drop by drop and extracted with ethyl acetate (2×8 l). The organic phases are washed consecutively with 0.5 N hydrochloric acid (1×4.3 l), water (1×4.4 l) and brine (1×4.4 l). The combined organic phases are dried over sodium sulfate (1.6 kg), filtered and boiled down in a rotary evaporator. By means of crystallization from ethyl acetate (1 l) and hexane (11 l) title compound Al is obtained from the residue as a white solid (656 g, 72%): $^1$H-NMR (400 MHz, DMSO-d$_6$, δ): 0.90–1.04 (m, 9H), 1.97 (m, 2H), 2.32 (m, 1H), 2.58 (m, 1H), 3.28 (s, 3H), 3.50 (m, 2H), 3.74 (s, 3H), 3.82 (q, 2H), 3.98 (m, 2H), 4.57 (m, 1H), 5.30 (d, 1H), 6.75–6.90 (m, 3H) ppm.

EXAMPLE A2

Preparation of

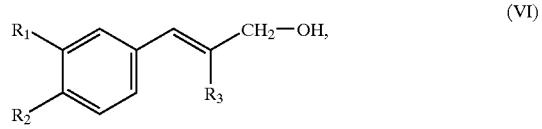

(A2)

A solution of 20 g Al and 0.4 g 4-dimethylaminopyridine in 100 ml tetrahydrofuran is cooled to 0° C., 6.3 ml acetic acid anhydride is added dropwise and the reaction mixture stirred for 1 hour. A solution of 19.0 g potassium t-butylate in 140 ml tetrahydrofuran is added drop by drop over a period of 30 minutes at −2° C. to 0° C. and then stirred for 2 hours at 0° C. Then 250 ml t-butyl methyl ether and 250 ml iced water are added to the reaction mixture. The organic phase is separated off and the aqueous phase extracted again with 250 ml t-butyl methyl ether. The organic phases are washed consecutively with 250 ml water and 250 ml brine. The combined organic phases are dried over magnesium sulfate (50 g), filtered and concentrated on a rotary evaporator. By means of flash chromatography (SiO$_2$ 60F/ethyl acetate/hexane 1:4) pure title compound A2 is obtained from the residue as a colourless oil (17.45 g, 92.6%): $^1$H-NMR (400 MHz, CDCl$_3$, δ): 1.26 (d, 6H), 1.35 (m, 3H), 2.15 (m, 2H), 3.22 (m, 1H), 3.38 (s, 3H), 3.60 (m, 2H), 3.90 (s, 3H), 4.17 (m, 2H), 4.28 (m, 2H), 6.85–7.0 (m, 3H), 7.49 (s, 1H) ppm.

EXAMPLE A3

Preparation of

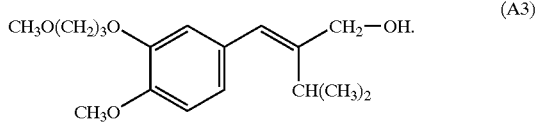

A solution of 37.0 g A2 in 410 ml toluene is cooled to −20° C., and 229 ml diisobutyl aluminium hydride solution (1.2 M in toluene) is added over a period of 20 minutes. The reaction mixture is stirred for 1 hour at −20° C., before 220 ml methanol is slowly added. Then 1.5 l 1N HCl is added to the mixture and this is then extracted with t-butyl methyl ether (3×1 l). The organic phases are washed consecutively with 1.2 l water and 1.2 l brine. The combined organic phases are dried over magnesium sulfate, filtered and concentrated on a rotary evaporator. By means of molecular distillation, title compound A3 is obtained from the residue as a colourless oil (29.7 g, 91.8%): $^1$H-NMR (400 MHz, DMSO-d$_6$, δ): 1.08 (d, 6H), 1.93 (m, 2H), 3.02 (m, 1H), 3.28 (s, 3H), 3.50 (m, 2H), 3.85 (s, 3H), 4.02 (m, 2H), 4.10 (d, 2H), 4.77 (bs, 1H), 6.39 (s, 1H), 6.78 (m, 2H), 6.93 (m, 1H) ppm.

EXAMPLE A4

Preparation of

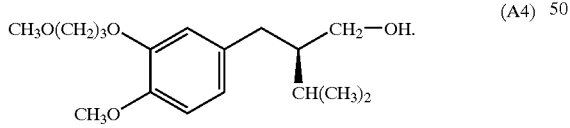

In a flask with a magnetic stirrer, 1.2 mg (0.0026 mmol) [Rh(norbornadiene)Cl]$_2$ and 3.83 mg (0.0054 mmol) (R)-(4,4',5,5',6,6'-hexamethoxybiphenyl-2,2'-diyl) bis (diphenylphosphine) are placed under an atmosphere of argon through repeated evacuation and purging with argon. Then 10 ml degassed toluene is added and stirred for 15 minutes, before 3.75 g (0.01275 mol) A3 and 20 ml degassed toluene are introduced into a 50 ml flask fitted with a stopcock and flushed with argon. With gentle heating, agitation is continued until a homogeneous solution is formed. The catalyst and substrate solutions are forced under pressure via a steel capillary tube into a 50 ml steel autoclave under cover of argon. In 3 purge cycles (argon 20 bar/hydrogen 20 bar) the hydrogen pressure is eventually increased to 1000 bar. The autoclave is heated to 30° C. and hydrogenation started by switching on the stirrer. The reaction can take place via hydrogen consumption (fall of pressure in the reservoir of hydrogen). After a reaction time of 18 hours, the reaction mixture is concentrated, and crude title compound A4 is obtained as a slightly yellowish oil (3.75 g, quantitative): The enantiomeric purity of the product (measured by HPLC: column Chiralcel ODH 0.46×25 cm; hexane/iPrOH: 95/5; temperature: 20° C.; flow rate: 0.6 ml/min; S-product: 22.9 min; R-product: 25.3 min; educt: 27.8 min; UV: 210 nm) amounts to >95% ee (R). $^1$H-NMR (400 MHz, CDCl$_3$, δ): 0.96 (m, 6H), 1.2 (m, 1H), 1.67 (m, 1H), 1.90 (m, 1H), 2.12 (m, 2H), 2.48 (m, 1H), 2.68 (m, 1H), 3.40 (s, 3H), 3.60 (m, 4H), 3.89 (s, 3H), 4.12 (m, 2H), 6.70–6.85 (m, 3H) ppm.

EXAMPLE A5

Preparation of A4

The procedure is analogous to that described under Example 1, but the ligand ((R)-(6,6'-dimethoxybiphenyl-2, 2'-diyl)-bis(dicyclobutylphosphine)) is used for the catalyst.

The reaction is stopped after 18 hours. The conversion amounts to 100%, and enantiomeric purity is 96.3% (R).

What is claimed is:

1. A process for the preparation of compounds of formula I,

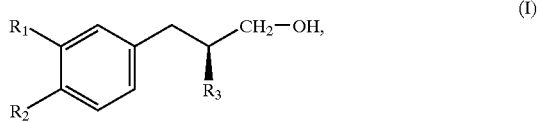

wherein R$_1$ and R$_2$ are independently of one another H, C$_1$–C$_6$alkyl, C$_1$–C$_6$halogenalkyl, C$_1$–C$_6$alkoxy, C$_1$–C$_6$alkoxy-C$_1$–C$_6$alkyl, or C$_1$–C$_6$-alkoxy-C$_1$–C$_6$alkyloxy, and R$_3$ is C$_1$–C$_6$alkyl comprising a) reacting compound of formula II

wherein R$_1$ and R$_2$ are as defined hereinbefore, with a compound formula III,

wherein R$_3$ is as defined hereinbefore, to form a compound of formula IV,

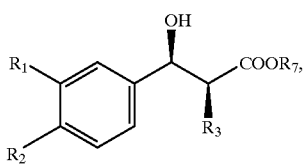

(IV)

wherein $R_7$ is $C_1$–$C_{12}$alkyl, $C_3$–$C_8$cycloaxyl, phenyl or benzyl, b) isolating a cristalline compound IV, acylating the OH group of the compound of formula IV to a leaving group, and eliminating the living group at low temperatures in the presence of an alkali metal alcoholate or a secondary amide in the reaction mixture of the acylation process to form a compound of formula V,

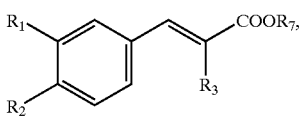

(V)

c) reducing the carbonic esters of formula V to form the alcohol of formula VI,

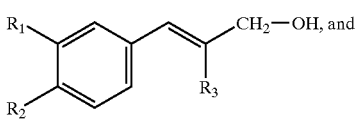

(VI)

d) hydrogenating the alcohol of formula VI in the presence of hydrogen and catalytic quantities of a metal complex as asymmetric hydrogenation catalyst, comprising metals from the group of ruthenium, rhodium and iridium, to which the chiral bidentate ligands are bonded, to form a compound of formula I.

2. A process according to claim 1, wherein $R_1$ is methoxy-$C_1$–$C_4$alkyloxy or ethoxy-$C_1$–$C_4$alkyloxy and $R_2$ is methoxy or ethoxy.

3. A process according to claim 2, wherein $R_1$ is 1-methoxyprop-3-yloxy and $R_2$ is methoxy.

4. A process according to claim 1, $R_3$ is a linear or branched $C_1$–$C_4$alkyl.

5. A process according to claim 4, wherein $R_3$ is isopropyl.

6. A process according to claim 1, wherein $R_1$ is 1-methoxy-n-propyloxy, $R_2$ is methoxy, and $R_3$ isopropyl.

7. A process according to claim 1, wherein step a) is carried out at low temperatures in the presence of a secondary lithium amide.

8. A process according to claim 1, wherein step b) is carried out by first acylation of the hydroxyl group and then elimination at low temperatures in the presence of an alkali metal alcoholate in the reaction mixture of the acylation process.

9. A process according to claim 1, wherein step c) is carried out at low temperatures in the presence of metal hydrides as reduction agents.

10. A process according to claim 1, wherein step d) is carried out in the presence of metal complexes of formula VII or VIIa as hydrogenation catalysts,

[LMeYZ] (VII)

[LMeY]$^+$E$^-$ (VIIa)

wherein

Me is rhodium;

Y stands for two olefins or one diene;

Z is Cl, Br or I;

E$^-$ is the anion of an oxygen acid or a complex acid; and

L is a chiral ligand from the ditertiary diphosphine group, in which the phosphine groups are bonded to a $C_2$–$C_4$ chain of the diphosphine backbone chain, and the diphosphine forms a five to seven-member ring together with the rhodium atom.

11. A process according to claim 10, wherein L is a group of formula VIII,

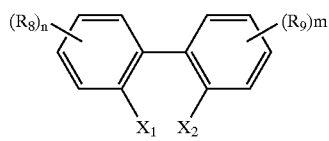

(VIII)

wherein m and n in each case are 0 or an integer from 1 to 4, and $R_8$ and $R_9$ are hydrogen or the same or different substituents, selected from $C_1$–$C_4$alkyl and $C_1$–$C_4$alkoxy; and $X_1$ and $X_2$ are, independently of one another, secondary phosphino.

12. A process according to claim 11, wherein the substituents are bonded in the 6 position or the 6,6' positions.

13. A process according to claim 11, wherein $R_8$ and $R_9$ are methyl, ethyl, methoxy or ethoxy.

14. A process according to claim 11, wherein the $X_1$ and $X_2$ groups are the same or different and correspond to formula —$PR_{10}R_{11}$, wherein $R_{10}$ and $R_{11}$ are the same or different and are branched $C_3$–$C_8$alkyl, $C_3$–$C_8$cycloaxyl, or unsubtituted phenyl or phenyl subtitute with one to three $C_1$–$C_4$alkyl, $C_1$–$C_4$alkoxy, or —$CF_3$.

15. A process according to claim 11, wherein in formulae VIII n is 0, and $X_1$ and $X_2$ are a $PR_{10}R_{11}$ group, wherein $R_{10}$ and $R_{11}$ in each case are cyclobutyl cyclopentyl, cyclohexyl, phenyl or phenyl substituted with 1 or 2 methyl, methoxy or $CF_3$.

16. A process according to claim 1, wherein step d) is carried out at temperatures of −20 to 150° C.

17. A process according to claim 1, wherein Step d) is carried out under positive pressure.

18. A process according to claim 1, which is carried out under pressure conditions at $10^5$ to $2\times10^7$ Pa (Pascal).

19. Compounds of formula VI,

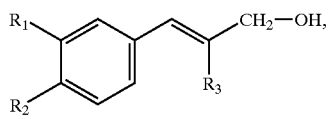

(VI)

wherein $R_1$ is methoxy-$C_1$–$C_4$alkyloxy or ethoxy-$C_1$–$C_4$alkyloxy, $R_2$ is methoxy or ethoxy, and $R_3$ is $C_1$–$C_6$alkyl.

20. Compounds according to claim 19, wherein $R_1$ is methoxy-$C_1$–$C_4$alkyloxy or ethoxy-$C_1$–$C_4$alkyloxy, $R_2$ is methoxyl or ethoxy, and $R_3$ $C_1$–$C_4$alkyl.

21. Compounds according to claim 19, wherein $R_1$ is 1-methoxy-n-propyloxy, $R_2$ is methoxy, and $_3$ is isopropyl.

22. Compounds of formula IV,

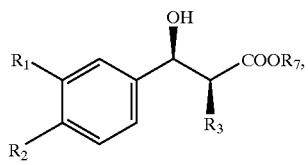

(IV)

wherein $R_1$ is methoxy-$C_1$–$C_4$alkyloxy or ethoxy-$C_1$–$C_4$alkyloxy, $R_2$ is methoxy or ethoxy, $R_3$ is $C_1$–$C_6$alkyl, and $_7$ is $C_1$–$C_{12}$alkyl, $C_3$–$C_8$cycloalkyl, phenyl or benzyl.

23. Compounds according to claim 22, wherein $R_1$ is methoxy-$C_1$–$C_4$alkyloxy or ethoxy-$C_1$–$C_4$alkyloxy, $R_2$ is methoxy or ethoxy, $R_3$ is $C_1$–$C_4$alkyl, and $R_7$ is $C_1$–$C_4$alkyl.

24. Compounds according to claim 22 wherein $R_1$ is methoxy-n-propyloxy, $R_2$ is methoxy, $R_3$ is isopropyl, and $_7$ is methyl or ethyl.

25. A process according to claim 12, wherein $R_8$ and $R_9$ are methyl, ethyl, methoxy or ethoxy.

* * * * *